United States Patent [19]
Kilpatrick

[11] Patent Number: 5,585,477
[45] Date of Patent: Dec. 17, 1996

[54] POLIOVIRUS SPECIFIC PRIMERS

[76] Inventor: David R. Kilpatrick, 488 Stonebridge Ct., Stone Mountain, Ga. 30083

[21] Appl. No.: 92,110

[22] Filed: Jul. 13, 1993

[51] Int. Cl.$^6$ ............................ C07H 21/02; C07H 21/04
[52] U.S. Cl. ...................................... 536/23.72; 536/24.33
[58] Field of Search ........................ 435/5, 91.2; 935/77, 935/78; 536/23.72, 24.33

[56] References Cited

U.S. PATENT DOCUMENTS

| | | | |
|---|---|---|---|
| 4,719,177 | 1/1988 | Baltimore et al. | 435/91.21 |
| 4,857,634 | 8/1989 | Minor et al. | 530/324 |

OTHER PUBLICATIONS

DeVear et al., J. Gen. Virol. 71:43–52 (1990) "Localization of genomic regions specific for the attenuated . . . ".

Abraham, R. et al., "Rapid detection of poliovirus by reverse transcription and polymerase chain amplication: Application for differentiation between poliovirus and nonpoliovirus enteroviruses", J. Clin. Micr. 31:395–399 (1993).

Balanant et al., "The natural genomic variability of Poliovirus analyzed by a restriction fragment length polymorphism assay", Virology 184:845–854 (1991).

Batzer, M. A. et al., "Enhanced evolutionary PCR using oligonucleotides with inosine at the 3'-terminus", Nucleic Acids Res., 19:5081 (1991).

Chapman, N. M. et al., "Molecular detection and identification of enteroviruses using enyzmatic amplification and nucleic acid hybridization", J. Clin. Micr. 28:843–850 (1990).

Hypia, T. et al., "Polymerase chain reaction for human picornaviruses", J. Gen. Virol. 70:3261–3268 (1989).

Kew, O. M. et al., "Evolution of the oral poliovaccine strains in humans occurs by both mutation and intramolecular recomination", In: R. Chanock and R. Lerner (Eds.), Modern approaches to vaccines, pp. 357–362. Cold Spring Harbor Laboratory, Cold spring Harbor, New York (1984).

Kew, O. M. et al., "Molecular epidemiology of wild poliovirus transmission", In: E. Kurstak, R. G. Marusyk, F. A., Murphy and M. H. V. Van Regenmortel (Eds.), Applied Virology Research, vol. 2, pp. 199–221. Plenum Press, New York (1990).

Ohtsuka, E. et al., "An alternative approach to deoxyoligonucleotides as hybridization probes by insertion of deoxyinosine at ambiguous codon positions", J. Biol. Chem. 260:2605–2608 (1985).

Olive, M. D. et al., "Detection and differentiation of picornairuses in clinical samples following genomic amplification", J. Gen. Virol. 71:2141–2147 (1990).

Palmenberg, A. C. et al., "Sequences of picornavirus capsid proteins", In: Molecular Aspects of Picornavirus Infection and Detection. Semler, B. and Ehrenfeld, E. (Eds.), ASM publications, pp. 215–230 (1989).

Stanway et al., "The Nucleotide Sequence of Poliovirus Type 3 leon 12 $a_1b$: Comparison With Poliovirus Type 1", Department of Microbiology: National Institute for Biological Standards and Controls, Nucleic Acids Research, vol. 11, 16:5629–5643 (1983).

Toyoda, H. et al., "Complete nucleotide sequences of all three poliovirus serotype genomes: Implication for genetic relationship, gene function and antigenic determinates", J. Mol. Biol. 174:561–585 (1984).

Yang, C.-F, De et al., "Detection and identification of vaccine–related polioviruses by the polymerase chain reaction", Virus Res. 20:159–179 (1991).

Yang, C.-F, De et al., "Genotype–specific in vitro amplification of sequences of the wild type 3 polioviruses from Mexico and Guatemala", Virus Research 24:277–296 (1992).

Girard, "Peptides Comprising An Immunogen Site of the Poliovirus and DNAs Containing Nucleotidic Sequences Coding for Said Peptides", WO88/03950, Jun. 2, 1988.

Primary Examiner—W. Gary Jones
Assistant Examiner—Eggerton Campbell

[57] ABSTRACT

The ability to rapidly detect wild polioviruses in clinical specimens is a major concern for the world-wide eradication of polioviruses. This report describes a method of detecting polioviruses of all three serotypes from viral isolates of clinical specimens using a pair of degenerate PCR primers. This primer set, which uses deoxyinosine residues to compensate for third position mismatches, recognizes nucleotide sequences near the receptor binding site of polioviruses. These sequences are unique to polioviruses and are absolutely conserved at the amino acid level. As a result, these PCR primers do not recognize nonpoliovirus enteroviruses. All poliovirus serotypes (40 poliovaccine related genotypes and 120 wild poliovirus genotypes from around the world) tested positive. All 14 prototype strains of nonpoliovirus enteroviruses tested negative. This "pan-poliovirus" degenerate PCR primer set will be useful in rapidly diagnosing poliovirus infections from world-wide clinical specimens.

5 Claims, No Drawings

POLIOVIRUS SPECIFIC PRIMERS

BACKGROUND OF THE INVENTION

1. Field of the Invention

This invention relates to polioviruses. In particular, this invention relates to poliovirus specific primers for detection of polioviruses in clinical samples.

2. Background Art

A worldwide endeavor sponsored by the World Health Organization is underway to eradicate all wild polioviruses by the year 2000, and virologic surveillance is therefore critical to this eradication goal. In 1990, an estimated 150,000 cases of poliomyelitis were occurring annually in 70 countries where the disease is still endemic. One of the primary goals to the global eradication of poliomyelitis by the year 2000 is in the intensive surveillance of acute flaccid paralysis (AFP) which can be caused by poliovirus. This is especially true in the Americas where the spread of the wild poliovirus has ceased for a period of at least two years. Nevertheless, 2400 cases of AFP in the first 40 weeks of 1992 needed to be screened for poliovirus. Of the 60 poliovirus related cases (3% of the total), none were the wild-type virus. Twenty percent (20%) of the total cases were found to be other non-polio enteroviruses (NPEV) and the remaining cases (76%) were negative for enteroviruses. Since the surveillance of wild-type poliovirus in AFP cases must be maintained at high levels, a detection system that would identify all polioviruses rapidly to the exclusion of NPEV is needed.

NPEVs also cause a wide range of diseases in addition to AFP and the ability to distinguish these cases from vaccine-related poliovirus cases would also be very beneficial. Currently, differentiation of poliovirus from nonpoliovirus is done by limited neutralization using three types of poliovirus antisera. This procedure is time consuming and sometimes has difficulties in identifying isolates containing mixtures of poliovirus and nonpoliovirus.

Poliovirus genomes evolve rapidly during replication in humans (Nottay et al., 1981; Minor et al., 1982). As a result, the nucleotide sequences of wild polioviruses currently in circulation throughout the world are extremely heterogeneous (Russ-Hess et al., 1987; Kew et al, 1990a). A typical rate for the fixation of mutations over the entire genome is one to two nucleotide substitutions per week (Nottay, et al., 1981). Although there may be a high degree of conservation at the amino acid level, there is considerable nucleotide variation. This variability occurs primarily by mutation to synonymous codons (Parvin et al., 1986), while immune selection pressures are responsible for some of this variability (Diamond et al., 1985; Blondel et al., 1986; Weigers and Dernick, 1992).

Independent wild poliovirus genotypes are usually geographically restricted (Kew et al., 1990a) and as a result, periodic epidemics involve the clonal expansion of this one restricted lineage. PCR primer sets for several wild poliovirus genotypes from the American regions have been previously described (Pan American Health Organization, 1990; Kew et al., 1990b; de Quadros et al., 1991; Yang et al.,. 1992). Similarly, primers have been developed which identify vaccine and reference strains of poliovirus (Yang et al., 1991; and Balanant et al., 1991). However, the molecular reagents currently in use do not allow for the rapid detection of all wild poliovirus genotypes in a single assay. Most of the PCR assays previously developed to detect either picornaviruses in general (Hyypia et al., 1989; Chapman et al., 1990;

Olive et al., 1990), or polioviruses specifically (Abraham et al., 1993) have targeted conserved sequences within the 5' noncoding region. PCR primers that are specific for the 5' noncoding region are subject to possible intertypic recombination, and therefore are not applicable to world-wide detection of polioviruses due to potential crossover problems. A large proportion of vaccine-related clinical isolates are intertypic recombinants (Kew and Nottay, 1984; Minor et al., 1986a).

Until genotype-specific primers and probes can be developed for all endemic wild polioviruses, a single specific assay system is needed that 1) detects wild poliovirus genotypes, from all geographic regions, including possibly undetermined geographic regions, and 2) distinguishes NPEV infections from poliovirus infections. The ability to differentiate between poliovirus and NPEV infections is of particular importance in those regions (such as the Americas) that no longer have wild poliovirus infections, but continue to have paralytic cases due to NPEVs.

Accordingly, the present invention provides a degenerate PCR primer designed to identify all three poliovirus serotypes, while not recognizing NPEVs. The primers of the present invention are specific for polioviruses, therefore excluding all other known viruses from detection. In addition to being specific for polioviruses, the primers of the present invention are capable of detecting all poliovirus strains so far tested in all three known serotypes.

The poliovirus-specific PCR primers and methods of detection of the present invention will allow for the rapid determination of whether clinical cases of acute flaccid paralysis are the result of a polio virus infection. Therefore, this invention meets an immediate need in the worldwide poliomyelitis eradication program, since these "pan-poliovirus" primers detect all genotypes of wild and vaccine related polioviruses.

SUMMARY OF THE INVENTION

The present invention provides isolated synthetic nucleic acids designed to be specific and sensitive for detecting all genotypes of poliovirus. Isolated nucleic acids complementary to the nucleic acids of the present invention are also provided. The present invention also provides compositions comprising the nucleic acids of the invention and nucleic acids capable of selectively hybridizing therewith.

The nucleic acids of the present invention can be utilized as degenerate primers and probes for the detection of a poliovirus in a sample utilizing a nucleic acid amplification technique. A method is also provided for detecting the presence or absence of a poliovirus in a sample containing nucleic acids which comprises amplifying the nucleic acids from the sample with the nucleic acids of the present invention and determining the presence or absence of nucleic acid from poliovirus, thereby detecting the presence or absence of poliovirus in the; sample. Further provided is a kit for detecting the nucleic acid of a poliovirus comprising primers comprised of nucleic acids provided by the present invention.

DESCRIPTION OF THE PREFERRED EMBODIMENTS

The present invention may be understood more readily by reference to the following detailed description of specific embodiments and the Examples, Tables and Sequence Listing included therein.

As used in the claims, "a" can mean one or more. The acronym "PCR" is used interchangeably with "polymerase chain reaction." The acronym "RT/PCR" is used interchangeably with "reverse transcriptase-polymerase chain reaction."

The present invention provides an isolated nucleic acid comprising the nucleotide sequence set forth in the Sequence Listing as SEQ ID NO:1. The consensus sequence set forth in SEQ ID NO:1 denotes the possible combinations of nucleotides that are found in SEQ ID NOS:5–12.

The present invention also provides an isolated nucleic acid complementary to the nucleotide sequence set forth in the Sequence Listing as SEQ ID NO:1. Also provided is a composition comprising a nucleic acid comprised of the nucleotide sequence set forth in the Sequence Listing as SEQ ID NO:1 and a nucleic acid that is capable of selectively hybridizing with that nucleic acid. By "selectively hybridizing" is meant that the nucleic acid does not hybridize with sequences from other enteroviruses to prevent adequate positive hybridization with nucleic acids from a poliovirus.

The present invention further provides an isolated nucleic acid comprising the nucleotide sequence set forth in the Sequence Listing as SEQ ID NO:2. The consensus sequence set forth in SEQ ID NO:2 denotes the possible combinations of nucleotides that are found in SEQ ID NOS:13–20.

The present invention also provides an isolated nucleic acid complementary to the nucleotide sequence set forth in the Sequence Listing as SEQ ID NO:2. Also provided is a composition comprising a nucleic acid comprised of the nucleotide sequence set forth in the Sequence Listing as SEQ ID NO:2 and a nucleic acid that is capable of selectively hybridizing with that nucleic acid.

In a further embodiment, the present invention provides a primer for the detection of a poliovirus in a sample utilizing a nucleic acid amplification technique, comprising the nucleotide sequence set forth in the Sequence Listing as SEQ ID NO:1. The primer of the present invention can be utilized as a degenerate primer comprised of one or more of the possible combinations of nucleotide sequences set forth in the Sequence Listing as SEQ ID NOS:5–12. It is contemplated by the present invention that the nucleic acids described herein can be utilized in any of a number of nucleic acid detection techniques including, but not limited to polymerase chain reaction, isothermal DNA amplification, etc. Likewise, the nucleic acid set forth in SEQ ID NO:1 can be used as a probe for detecting or capturing a nucleic acid which hybridizes with the nucleic acid of SEQ ID NO:1.

The present invention also provides a primer for the detection of a poliovirus in a sample utilizing a nucleic acid amplification technique, comprising the nucleotide sequence set forth in the Sequence Listing as SEQ ID NO:2. The primer set forth in SEQ ID NO:2 can be utilized as a degenerate primer comprised of one or more of the possible combinations of nucleotide sequences set forth in the Sequence Listing as SEQ ID NOS:13–20. Similarly, the nucleic acid set forth in SEQ ID NO:2 can be used as a probe for detecting or capturing a nucleic acid which hybridizes with the nucleic acid of SEQ ID NO:2.

It is also contemplated by the present invention that any of the primers or probes described herein can be labeled or tagged for use in e.g., chemiluminescent or fluorescent detection systems.

In a further embodiment, the present invention provides a method for detecting the presence or absence of a poliovirus in a sample containing nucleic acids comprising the steps of:

a) amplifying the nucleic acids from the sample with a primer pair comprised of a primer comprising the nucleotide sequence set forth in the Sequence Listing as SEQ ID NO:1 and a suitable upstream primer;

b) determining the presence or absence of a nucleic acid from poliovirus, thereby detecting the presence or absence of poliovirus in the sample. As used herein, a "suitable upstream primer" is any of the possible primers which can be designed from known sequences for the VP1 gene located upstream (i.e. 5') of position number 2914 following the numbering system of Kew et al., (1990a). Examples of a suitable upstream primer include, but are not limited to the Panpv 2S and Panpv 13S primers described herein.

In one embodiment, the invention provides a method for detecting the presence or absence of a poliovirus in a sample containing nucleic acids comprising the steps of:

a) amplifying the nucleic acids from the sample with a primer pair comprised of a primer comprising the nucleotide sequence set forth in the Sequence Listing as SEQ ID NO:1 and a primer comprising the nucleotide sequence set forth in the Sequence Listing as SEQ ID NO:2;

b) determining the presence or absence of a nucleic acid from poliovirus, thereby detecting the presence or absence of poliovirus in the sample.

Also provided by the present invention is a kit for detecting a nucleic acid of a poliovirus by nucleic acid amplification comprising a primer comprised of the nucleotide sequence set forth in the Sequence Listing as SEQ ID NO:1 and a suitable upstream primer. In one embodiment the invention provides a kit for detecting a nucleic acid of a poliovirus by nucleic acid amplification comprising a primer comprised of the nucleotide sequence set forth in the Sequence Listing as SEQ ID NO:1 and a primer comprising the nucleotide sequence set forth in the Sequence Listing as SEQ ID NO:2.

The nucleic acid specific for each genotype of poliovirus can be detected utilizing a nucleic acid amplification technique, such as polymerase chain reaction (PCR) as taught in the examples described herein. Alternatively, the nucleic acid is detected utilizing direct hybridization or by utilizing a restriction fragment length polymorphism. For example, the present invention contemplates a :method of detecting the presence of all poliovirus genotypes to the exclusion of nonpolio enteroviruses. PCR primers which hybridize only with nucleic acids specific for a target sequence (e.g., SEQ ID NO:3) of the poliovirus can be utilized. The presence of amplification indicates the presence of the virus. Alternatively, the poliovirus can be detected by directly hybridizing the target sequence with a nucleic acid probe selective for the specific target sequence of the poliovirus.

Polymerase chain reaction (PCR) and RT/PCR are examples of techniques that amplify specific nucleic acid sequences with remarkable efficiency. Repeated cycles of denaturation, primer annealing and extension carried out with a polymerase, e.g., the heat stable enzyme Taq polymerase, leads to exponential increases in the concentration of desired nucleic acid sequences. Given a knowledge of the appropriate target nucleic acid sequence of the poliovirus as provided by the present invention, synthetic oligonucleotides can be prepared which are complementary to all of the possible sequences in the poliovirus of interest. Each oligonucleotide primer species is complementary to one of the possible poliovirus specific degenerate sequences of interest. The nucleic acid can be denatured at high temperatures (e.g., 95° C.) and then reannealed in the presence of a large molar excess of the oligonucleotides. The oligonucleotides, oriented with their 3' ends pointing towards each other, hybridize to opposite strands of the target sequence and prime enzymatic extension along the nucleic acid template in the presence of the four deoxyribonucleotide triphosphates. The end product is then denatured again for another cycle. After this three-step cycle has been repeated several times, amplification of a nucleic acid segment by more than one million-fold can be achieved. The resulting nucleic acid may then be directly detected by any of a number of methods well known in the art (for example, Southern blotting using poliovirus specific probes as descried above).

In general, primers for PCR are usually about 20 bp in length and the preferable range is from 15–25 bp. Better amplification is obtained when both primers are the same length and with roughly the same nucleotide composition. Denaturation of strands usually takes place at about 94° C. and extension from the primers is usually at about 72° C. The annealing temperature varies according to the sequence under investigation. Examples of reaction times are: 20 mins denaturing; 35 cycles of 2 min, and 1 min, 1 min for annealing, extension and denaturation; respectively and finally, a 5 min extension step.

The present invention is more particularly described in the following examples which are intended as illustrative only since numerous modifications and variations therein will be apparent to those skilled in the art.

EXAMPLES

Viruses

Poliovirus isolates (Tables 1 and 2) have been previously characterized by neutralization with hyperimmune equine sera and partial genomic sequencing (Rico-Hesse et al., 1987; Kew et al 1990a; De et al., in preparation). Vaccine-related strains were also positively identified by PCR using the Sabin strain-specific primer pairs (Yang et al., 1991). Fourteen human nonpolio enteroviruses were identified by confirmation of serotype with monotypic neutralizing polyclonal antibodies. Viruses were propagated in HeLa or RD monolayers to produce high-titer inoculation stocks.

TABLE 1

Vaccine-Related Poliovirus Genotypes Detected by Pan-Polio PCR

Type 1

| 0584/GUT91 | 0246/GUT90 | 9825/USA89 | 9703/ELS89 |
| --- | --- | --- | --- |
| 9360/VEN89 | 9240/HON89 | 2800/H0N91 | 8315/MEX88 |
| 6258/MOR85 | 5498/USA84 | | |

Type 2

| 0636/ELS91 | 0042/ELS90 | 9897/GUT90 | 0078/PER89 |
| --- | --- | --- | --- |
| 9818/PER89 | 9519/USA89 | 8370/PER88 | 8018/GUT87 |
| 7653/SOA86 | 7170/MEX86 | 6700/HON86 | 7837/PER84 |
| 6886/GUT83 | | | |

Type 3

| 1063/USA91 | 0644/HON91 | 0642/ELS91 | 0405/GUT90 |
| --- | --- | --- | --- |
| 0040/ELS90 | 0131/MEX89 | 0044/GUT89 | 9896/GUT89 |
| 9442/NIC89 | 9441/GUT89 | 8774/TRT88 | 1339/CHN89 |
| 8239/GUT87 | 6880/COL86 | | |

TABLE 2

Wild Poliovirus Genotypes Detected by Pan-Polio PCR

Type 1

| 0006/CHN89 | 0109/CHN86 | 0032/CHN91 | 0124/CHN91 |
| --- | --- | --- | --- |
| 0285/INO86 | 0289/POR87 | 0427/SSR91 | 0440/SSR90 |
| 0467/COL89 | 0941/SRL87 | 0955/SRL88 | 1184/ROM91 |
| 1187/ROM91 | 1338/CHN89 | 1607/SOA88 | 2609/ETH91 |
| 2611/PAK90 | 2662/COL87 | 2758/SVN89 | 2786/VTN90 |
| 2854/HON91 | 3638/CHN85 | 3643/CHN91 | 3647/CHN91 |
| 3677/CYP92 | 3706/MAA92 | 3907/PHL91 | 3940/THA92 |
| 6224/ZIM85 | 6536/NEP86 | 6700/TUR90 | 6701/TUR90 |
| 6750/SEN86 | 7054/IND86 | 7169/BUL91 | 7362/PAK91 |
| 7377/BOL86 | 8223/GUT87 | 8425/ISR88 | 8644/IND91 |
| 8645/IND92 | 8649/IND91 | 8771/OMA88 | 9366/SAA89 |
| 9475/ZAI89 | 05145/UZB88 | 07470/TOG92 | 09323/MOG91 |
| 11231/EGY91 | 11236/EGY91 | 11267/EGY91 | 11270/EGY91 |
| 15949/FRA89 | 16834/TUR90 | 16838/TUR90 | 18641/PAK91 |
| 18655/PAK91 | | | |

Type 2

| 0290/TUR73 | 0291/TUR73 | 0295/ISR78 | 0297/KUW78 |
| --- | --- | --- | --- |
| 0298/EGY79 | 0302/YUG81 | 0305/IRA71 | 1155/ALB91 |
| 1534/IND82 | 2613/PAK89 | 2710/KEN71 | 6876/COL86 |
| 7079/IND82 | 7354/PAK91 | 8650/IND91 | 8654/IND91 |
| 05144/UZB88 | 11263/EGY91 | 18637/PAK91 | 18638/PAK91 |

Type 3

| 0314/ROM80 | 0380/MEX90 | 0426/SSR90 | 0672/OMA91 |
| --- | --- | --- | --- |
| 2615/MOL90 | 2619/MOL90 | 2723/TUR90 | 2728/ARM90 |
| 2731/URZ89 | 4075/ARM90 | 6184/FIN84 | 7095/IND86 |
| 7350/PAK91 | 7377/BOL86 | 8178/VEN87 | 8668/IND91 |
| 8670/IND91 | 9035/BRA88 | 9259/TUN88 | 05141/UZB88 |
| 05142/UZB88 | 11246/EGY91 | 11252/EGY91 | 11257/EGY91 |
| 15952/FRA90 | 16837/TUR90 | 18643/PAK91 | 18653/PAK91 |

Oligonucleotide Synthesis

Synthetic oligodeoxynucleotides were prepared, purified, and analyzed as described (Yang et al., 1991). The degenerate primers used for amplifying poliovirus are:

Panpv 1A (A:2915–2934) 5'-TTIAIIGC(AG)TGICC(AG)T-T(AG)TT-3' (SEQ ID NO:1)

Panpv 2S (S:2852–2871) 5'-TTCAC(AC)TAIT-CIAG(N)TTTGA-3' (SEQ ID NO:21)

Panpv 13S (S:2852–2871) 5'-TTCAC(AC)TAITCI(AC)G-ITT(TC)GA-3' (SEQ ID NO:2)

The numbers in parentheses indicate the genomic intervals matching the primers (A=antigenome polarity primer; S=sense or genome polarity primer; following the numbering system of Kew et al. (1990a). Primer Panpv 1A as used herein refers to the consensus sequence set forth in the sequence listing as SEQ ID NO:1. The eight possible primer species for the consensus sequence SEQ ID NO:1 are set forth in the Sequence Listing as SEQ ID NOS:5–12. Primer Panpv 13S as used herein refers to the consensus sequence set forth in the Sequence Listing as SE0 ID NO:2. The eight possible primer species for the consensus sequence SEQ ID NO:2 are set forth in the Sequence Listing as SEQ ID NOS:13–20. Primer Panpv 2S as used herein refers to the consensus sequence set forth in the Sequence Listing as SEQ ID NO:21.

PCR Amplification and Analysis

In vitro amplification by PCR was performed as described previously (Yang et al., 1992). Amplification reactions were carried out in 50 μl reaction mixtures containing 1 μl of each individual virus tissue culture lysate in 50 mM Tris-HCl (pH 8.3), 70 mM KCl, 5 mM MgCl$_2$, 10 mM dithiothreitol, 10 pmol of each primer, 200 μM each of dATP, dCTP, dCTP, dTTP (Pharmacia), 0.5% NP-40, 10 U placenta ribonuclease inhibitor (Boehringer Mannheim Biochemicals, Indianapolis, Ind.), 2.5 U AMV reverse transcriptase (Boehringer Mannheim), and 2.5 U of Taq DNA polymerase (Perkin Elmer-Cetus, Norwalk, Conn.). The reaction mixtures were prepared, excluding the ribonuclease inhibitor, AMV reverse transcriptase, and Taq DNA polymerase, overlaid with mineral oil, heated for 5 min at 95° C. to release the virion RNA and chilled on ice. The enzymes were then added and the samples incubated at 42° C. for 30 min before 30 cycles of programmed amplification (denaturation:94° C., 1 min; annealing: 42° C., 1 min; extension:60° C., 1 min) in a DNA thermal cycler (Perkin Elmer-Cetus). Conditions for polyacrylamide gel electrophoresis, and detection of amplified products by ethidium bromide staining were as described (Yang et al., 1991).

Selection of Primer Binding Sites

The amino acid alignment in the capsid protein region (Palmenberg, 1989) of a wide variety of picornaviruses was used to find poliovirus amino acid residues that were near residues suspected to be involved in receptor attachment/recognition and conserved among only picornaviruses. A 7 amino acid sequence in VP1 (NNGHALN, as set forth in the Sequence Listing as SEQ ID NO:3) that was unique to only polioviruses was chosen as a possible PCR primer site. A degenerate PCR primer (anti-sense; designated as Panpv 1A) was designed using this sequence information as well as possible nucleotide incorporation at the first and third codon positions due to codon degeneracy. Deoxyinosine residues were used in those positions where 3 or 4 different nucleotides were possible. This was done to keep the number of possible primer species at a minimum. Since there are 8 possible species of Panpv 1A (SEQ ID NOS:5–12), a concentration of 80 picomoles was used per reaction (10 pM/primer species). Similarly, another 7 amino acid (FTYSRFD, as set forth in the Sequence Listing as SEQ ID NO:4) sequence was located upstream from Panpv 1A and chosen as the sense PCR primer site (designated as Panpv 2S). This PCR primer set yields an 83 bp PCR product. We generally use primer pairs that are closely spaced (<250 nucleotides) along the template because AMV reverse transcriptase has relatively low processivity (Berger et al., 1983). Diagnostic sensitivities are generally improved by reducing the lengths of the cDNA transcripts required to initiate the chain reactions.

Detection of Vaccine-Related Polioviruses

The Panpv 1A/2S primer pair was first tested against different vaccine-related poliovirus genotypes since they would have the least amount of nucleotide sequence heterogeneity. One microliter of each infected tissue culture lysate was amplified in an RT/PCR reaction mixture. After 30 amplification cycles, DNA products were separated by electrophoresis on 12% polyacrylamide gels and visualized the ethidium bromide staining. A single 83 bp product was seen from all samples. The remaining vaccine-related isolates also yielded this same 83 bp product. A wide range of genotypes from around the world and representing all three serotypes was also tested. All of the isolates tested positive (Table 1).

Detection of Wild Polioviruses

Poliovirus genomes evolve rapidly during replication in humans. However, the 7 amino acid sequences set forth in SEQ ID NO:3 were found to be absolutely conserved in the 23 complete VP1 nucleotide sequences presently in the Centers for Disease Control and Prevention data base. An 83 bp PCR product was found when 13 wild type 1 poliovirus isolates were tested with the Panpv 1A/2S primer set. Subsequently, all 120 poliovirus isolates (Table 2) were found to be positive. This :suggests that the NNGHALN amino acid sequence is conserved among all polioviruses. However, in six isolates a weak PCR product was detected. This was thought to be a result of poor primer homology due to the upstream Panpv 2S primer. Further analysis found that in some instances the minus 3 and minus 8 positions from the 3'-terminus of the 2S primer do not correctly match the virus sequence (for example isolate 9288/MEXVP1 has a C at positions minus 3 and minus 8). Proper annealing at the 3' end of the primer is known to be very important to the fidelity of Taq polymerase in extending the sequence. Panpv 2S was re-designed to contain a T or C at the minus 3 position and an A or C at the minus 8 position to see if this would increase the yield of the PCR product (since the nucleotide sequences for these isolates was unknown). A deoxyinosine residue was also introduced at the minus 6 position to reduce the number of primer species. This new primer, Panpv 13S was used along with Panpv 1A to amplify the isolates which gave the weakest priming. The results showed a stronger PCR product when this new primer was used, as compared to the original Panpv 2S primer. This indicates that the weaker PCR product found with a few virus isolates is due to poor annealing of the Panpv 2S primer and noir to weak annealing of Panpv 1A.

Specificity

The primary need for developing poliovirus specific PCR is to rapidly distinguish poliovirus cases of acute flaccid paralysis (AFP) from NPEV cases of AFP. This is becoming increasingly important in the surveillance of AFP cases in those areas of the world that have essentially eliminated wild poliovirus. When the Panpv 1A/2S primer pair was tested against a wide range of nonpoliovirus enteroviruses, no amplification products were detected. These data supported our early hypothesis that the NNGHALN amino acid sequence in VP1 is unique among all polioviruses. To prove that each isolate tested did indeed contain viable virus, these same isolates were tested with an enterovirus specific primer pair (EV/PCR-1 & EV PCR-2). This primer pair recognizes highly conserved nucleotide sequences in the 5' noncoding region in a wide range of enteroviruses (Yang et al., 1992). The expected 114 bp PCR product of the enterovirus primer pair was identified in all of the isolates tested. This indicates that the Panpv 1A/2S primer pair is specific for polioviruses and does not recognize other enteroviruses.

Detection of Poliovirus in an Isolate Typed as NPEV

Virus isolates are presently typed as NPEV by their ability to replicate in the presence of neutralizing antisera specific to polioviruses. However, low titers of poliovirus can be masked by the presence of higher NPEV titers. Such a case was suspected due to uncharacteristic growth in tissue culture during typing. Two suspected poliovirus cases originally typed as NPEV were tested with the Panpv 1A/2S primer set. The 83 bp PCR product characteristic of the primer pair was detected and clearly indicated the presence of poliovirus. A serotype 1 poliovirus was eventually isolated from this sample. This shows that the pan-poliovirus PCR primer set would be very useful in rapidly distinguishing poliovirus from NPEV in samples containing both virus types.

Throughout this application, various publications are referenced by author and year. The disclosures of these publications in their entireties are hereby incorporated by reference into this application in order to more fully describe the state of the art to which this invention pertains. A complete reference citation is provided below.

Although the present process has been described with reference to specific details of certain embodiments thereof, it is not intended that such details should be regarded as limitations upon the scope of the invention except as and to the extent that they are included in the accompanying claims.

REFERENCES

Abraham, R., Chonmaitree, T., McCombs, J., Prabhakar, B., Lo Verde, P. T. and Ogra, P. L. (1993). Rapid detection of poliovirus by reverse transcription and polymerase chain amplification: Application for differentiation between poliovirus and nonpoliovirus enteroviruses.

Balanant et al. (1991). The natural genomic variability of Poliovirus analyzed by a restriction fragment length polymorphism assay. Virology 184, 845–854.

Batzer, M. A., Carlton, J. E., and Deininger, P. L. (1991). Enhanced evolutionary PCR using oligonucleotides with inosine at the Y-terminus. Nucleic Acids. Res. 19, 5081.

Blondel, B., Crainic, R., Fichot, O., Dufraisse, G., Candrea, A., Diamond, D., Girard, M., and Horaud, F. (1986). Mutations conferring resistance to neutralization with monoclonal antibodies in type 1 poliovirus can be located outside or inside the antibody binding site. J. Virol. 57, 81–90.

Chapman, N. M., Tracy, S., Gauntt, C. J. and Fortmueller, U. (1990). Molecular detection and identification of enteroviruses using enzymatic amplification and nucleic acid hybridization. J. Clin. Micr. 28, 843–850.

Chow, M., Yabrov; R., Bittle, J., Hogle, J. and Baltimore, D. (1985). Synthetic peptides from four seperate regions of the poliovirus type 1 capsid protein VP1 induce neutralizing antibodies. Proc. Natl. Acad. Sci. USA 82, 910–914.

de Qaudros, C. A., Andurs, J. K., Olive, J.-M., da Silveira, C. M., Eikhoff, R. M., Carrasco, P., Fitzsimmons, J. W. and Pinheiro, F. P. (1991). Eradications of poliomyelitis: progress in the Americas. Pediatr. Inf. Dis. J. 10, 222–229.

Diamond, D. C., Jameson, B. A., Bonin, J., Kohara, M., Abe, S., Itoh, H., Komatsu, T., Arita, M., Kuge, S., Nomoto, A., Osterhaus, A. D. M. E., Crainic, R., and Wimmer, E. (1985). Antigenic variation and resistance to neutralization in poliovirus type 1. Science 229, 1090–1093.

Evans, D. M., Minor, P. D., Schild, G. C., and Almond, J. W. (1983). Critical role of an eight amino acid sequence of VP1 in neutralization of poliovirus type 3. Nature 304, 439–462.

Giranda, V. L., Chapman, M. S. and Rossman, M. G. (1990). Modeling of the human intercellular adhesion molecule-1, the human rhinovirus major group receptor.

Heinz, B. A., Shepard, D. A., Rueckert, R. R. (1989). Drug-resistant mutants of human rhinoviruses map to capsid regions involved in attachment. In: Europic 89. (abstr. no. G10).

Hogle, J. M., Chow,, M., Filman, D. J. (1985). Three-dimensional structure of poliovirus at 2.9 A resolution. Science 229, 1358–1365.

Hyypia, T., Auvinen, P. and Maaronen, M. (1989). Polymerase chain reaction for human picornaviruses. J. Gen. Virol. 70, 3261–3268.

Ketterlinus, R., Wiegers, K. and Dernick, R. (1993). Revertants of poliovirus escape mutants: New insights into antigenic structures. Virol. 192, 525–533.

Kew, O. M. and Nottay, B. K. (1984). Evolution of the oral poliovaccine strains in humans occurs by both mutation and intramolecular recombination. In: R. Chanock and R. Lerner (Eds.), Modern approaches to vaccines, pp. 357–362. Cold Spring Harbor Laboratory, Cold Spring Harbor, N.Y.

Kew, O. M., Nottay, B. K., Rico-Hesses, R. R. and Pallanseh, M. A. (1990a). Molecular epidemiology of wild poliovirus transmission. In: E. Kurstak, R. G., Marusyk, F. A., Murphy and M. H. V. Van Regenmortel (Eds.), Applied virology research, Vol. 2, pp. 199–221. Plenum Press, New York.

Kew, O. M., Pallansch, M. A., Nottay, B. K., Rico-Hesse, R. R., De, L. and Yang, C.-F. (1990b). Genotypic relationships among wild polioviruses from different regions of the world. In: M. A. Brinton and F. X. Heinz (Eds.), New Aspects of Positive-Strand RNA Viruses. pp. 357–365. American Society for Microbiology, Washington, D.C.

King, A. M. Q. (1988). Preferred sites of recombination in poliovirus RNA: an analysis of 40 intertypic cross-over sequences. Nucleic Acids Res. 16, 11705–11723.

Lentz, T. L. (1990). Review article: The recognition event between virus and host cell receptor, a target for antiviral agents. J. Gen. Virol. 71, 751–766.

Mendelsohn, C., Johnson, B., Lionetti, K. A., Nobis, P., Wimmer, E., Racaniello, V. R. (1986). Transformation of a human poliovirus receptor gene into mouse cells. Proc Natl. Acad. Sci. USA 83, 7845–7849.

Mendelsohn, C., Wimmer, E., Racaniello, V. R. (1989). Cellular receptor for poliovirus: molecular cloning, nucleotide sequence and expression of a new member of the immunoglobulin superfamily. Cell 56, 855–865.

Minor, P. D., Schild, G. C., Ferguson, M., Mackay, A., Magrath, D. I., John, A., Yates, P. J., and Spitz, M. (1982). Genetic and antigenic variation in type 3 polioviruses: Characterization of strains by monoclonal antibodies and T1 oligonucleotide mapping. J. Gen. Vir. 61, 167–176.

Minor, P. D., Schild, G. C., Bootman, J., Evans, D. M. A., Ferguson, M., Reeve, P., Spitz, M., Stanway, F., Cann, A. J., Hauptmann, R., Clarke, L.-D., Mountford, R. C., and Almond, J. W. (1983). Location and primary structure of a major antigenic site for poliovirus neutralization. Nature 301, 674–679.

Minor, P. D., Pipkin, P. A., Hockley, D., Schild, G. C. Almond, J. W. (1984). Monoclonal antibodies which block cellular receptors of poliovirus. Virus Research 1, 203–212.

Minor, P. D., Ferguson, M. and Icenogle, J. P. (1986a). Antigenic and molecular evolution of the vaccine strain of type 3 poliovirus during the period of excretion by a primary vaccinee. J. Gen. Virol. 67, 693–706.

Minor, P. D., Ferguson, M., Evans, D. M. A., Almond, J. W., and Icenogle, J. P. (1986b). Antigenic structure of polioviruses of serotypes 1, 2, and 3. J. Gen. Virol. 67, 1283–1291.

Nobis, P., Zibirre, R., Meyer, G., Kuhne, J., Warnecke, G., Koch, G. (1985). Production of a monoclonal antibody against an epitope on HeLa cells that is the functional poliovirus binding site. J. Gen. Virol. 6, 2563–2569.

Nottay, B. K., Kew, O. M., Hatch, M. H., Heyward, J. T., and Obijeski, J. F., (1981). Molecular variation of type 1 vaccine-related and wild polioviruses during replication in humans. Virology 108, 405–423.

Ohtsuka, E., Matsuki, S., Ikehara, M., Takahasi, Y., and Matsubara, K. (1985). An alternative approach to deoxyoligonucleotides as hybridization probes by insertion of deoxyinosine at ambiguous codon positions. J. Biol. Chem. 260, 2605–2608.

Olive M. D., Al-Mufti, S., Al-Mulla, W., Khan, M. A., Pasca, A., Stanway, G. and Al-Nakib, W. (1990). Detection and differentiation of picornaviruses in clinical samples following genomic amplification. J. Gen. Virol. 71, 2141–2147.

Page, G. S., Mosser, A. G., Hogle, J. M. Filman, D. J., Rueckert, R. R., and Chow, M. (1988). Three-dimensional structure of poliovirus serotype 1 neutralizing determinants. J. Virol. 62, 1781–1794.

Palmenberg, A. C. (1989). Sequences of picornavirus capsid proteins. In: Molecular Aspects of Picornavirus Infection and Detection. Semler, B. and Ehrenfeld, E. (Eds.), ASM publications, pp. 215–230.

Pan American Health Organization, Washington (1990). Surveillance of wild poliovirus in the Americas. EPI Newsl. 12, 1–3.

Pan American Health Organization, Washington (1991 and 1992). Expanded program on immunization in the Americas. Vol XIV, #5 & #6.

Parvin, J. D., Moscona, A., Pan, W. T., Leider, J. M. and Palese, P. (1986). Measurement of the mutation rates of animal viruses: Influenza A virus and poliovirus type 1. J. Virol. 59, 377–383.

Rico-Hesse, R., Pallansch, M. A., Nottay, B. K., and Kew, O. M. (1987). Geographic distribution of wild poliovirus type 1 genotypes. Virology 160, 311–322.

Rossman, M. G., Arnold, E., Erickson, J. W., Frankenberger, E. A., Griffith, J. P., Hech, H.-J., Johnson, J. E., Kamer, G., Luo, M., Mosser, A. G., Rueckert, R. R., Sherry, B. and Vriend G. (1985). Structure of a human common cold virus and functional relationship to other picornaviruses. Nature 317, 145–153.

Rossman, M. G. and Palmenberg, A. C. (1989). Conservation of the putative receptor attachment site in picornaviruses. Virol. 164, 373–382.

Shepley, M. P., Sherry, B., Weiner, H. L. (1988). Monoclonal antibody identification of a 100 kDa membrane protein in HeLa cells and human spinal cord involved in poliovirus attachment. Proc. Natl. Acad. Sci. USA 85, 7743–7747.

Toyoda, H., Kohara, M., Katoaka, Y., Suganuma, T., Omata, T., Imura, N., and Nomoto, A. (1984). Complete nucleotide sequences of all three poliovirus serotype genomes: Implication for genetic relationship, gene function and antigenic determinants. J. Mol. Biol. 174, 561–585.

Weigers, K., Uhlig, H., and Dernick, R. (1988). Evidence of a complex structure of neutralization antigenic site 1 of poliovirus type 1 Mahoney. J. Virol. 62, 1845–1848.

Weigers, K., Uhlig, H., and Dernick, R. (1989). N-Ag IB of poliovirus type 1: A discontinuous epitope formed by two loops of VP1 comprising residues 96–104 and 141–152. Virology 70, 583–586.

Wiegers, K. J., and Dernick, R. (1992). Molecular basis of antigenic structures of poliovirus: Implications for their evolution during morphogenesis. J. Virol. 66, 4597–4600.

Yang, C.-F., De, L., Holloway, B. P., Pallansch, M. A., and Kew, O. M. (1991). Detection and identification of vaccine-related polioviruses by the polymerase chain reaction. Virus Res. 20, 159–179.

Yang, C.-F., De, L., Yang, Su-Ju, Gomez, J. R., Cruz, J. R., Holloway, B. P., Pallansch, M. A. and Kew, O. M. (1992). Genotype-specific in vitro amplification of sequences of the wild type 3 polioviruses from Mexico and Guatemala. Virus Research 24, 277–296.

---

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Other nucleic acid ( i v ) ANTI-SENSE: YES ( i x ) FEATURE:
        ( A ) NAME/KEY: misc_feature
        ( B ) LOCATION: 1..20
        ( D ) OTHER INFORMATION: /product= "Synthetic DNA"
        / note= "In the primer sequence submitted N=inosine; R=A
        or G; and nucleotide # for the entire sequence is
        2915- 2934."

( x i ) SEQUENCE DESCRIPTION: SEQ ID NO:1:

TTNANNGCRT GNCCRTTRTT                           20

( 2 ) INFORMATION FOR SEQ ID NO:2:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: Other nucleic acid ( i v ) ANTI-SENSE: NO ( i x ) FEATURE:
    ( A ) NAME/KEY: misc_feature
    ( B ) LOCATION: 1..20
    ( D ) OTHER INFORMATION: /product= "Synthetic DNA"
      / note= "In the primer sequence submitted N=inosine; M=A
      or C; Y=T or C; and nucleotide # for the entire sequence
      is 2852- 2871."

( x i ) SEQUENCE DESCRIPTION: SEQ ID NO:2:

TTCACMTANT CNMGNTTYGA                                           20

( 2 ) INFORMATION FOR SEQ ID NO:3:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:3:

Asn  Asn  Gly  His  Ala  Leu  Asn
    1                   5

( 2 ) INFORMATION FOR SEQ ID NO:4:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:4:

Phe  Thr  Tyr  Ser  Arg  Phe  Asp
    1                   5

( 2 ) INFORMATION FOR SEQ ID NO:5:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: Other nucleic acid ( i v ) ANTI-SENSE: YES ( i x ) FEATURE:
    ( A ) NAME/KEY: misc_feature
    ( B ) LOCATION: 1..20
    ( D ) OTHER INFORMATION: /product= "Synthetic DNA"
      / note= "In the primer sequence submitted N=inosine; and
      nucleotide # for the entire sequence is 2915-2934."

( x i ) SEQUENCE DESCRIPTION: SEQ ID NO:5:

TTNANNGCGT GNCCGTTGTT                                           20

( 2 ) INFORMATION FOR SEQ ID NO:6:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: Other nucleic acid ( i v ) ANTI-SENSE: YES ( i x ) FEATURE:
      ( A ) NAME/KEY: misc_feature
      ( B ) LOCATION: 1..20
      ( D ) OTHER INFORMATION: /product= "Synthetic DNA"
         / note= "In the primer sequence submitted N=inosine; and
         nucleotide # for the entire sequence is 2915-2934."

( x i ) SEQUENCE DESCRIPTION: SEQ ID NO:6:

TTNANNGCAT GNCCGTTGTT                                                                 20

( 2 ) INFORMATION FOR SEQ ID NO:7:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: Other nucleic acid ( i v ) ANTI-SENSE: YES ( i x ) FEATURE:
      ( A ) NAME/KEY: misc_feature
      ( B ) LOCATION: 1..20
      ( D ) OTHER INFORMATION: /product= "Synthetic DNA"
         / note= "In the primer sequence submitted N=inosine; and
         nucleotide # for the entire sequence is 2915-2934."

( x i ) SEQUENCE DESCRIPTION: SEQ ID NO:7:

TTNANNGCAT GNCCATTGTT                                                                 20

( 2 ) INFORMATION FOR SEQ ID NO:8:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: Other nucleic acid ( i v ) ANTI-SENSE: YES ( i x ) FEATURE:
      ( A ) NAME/KEY: misc_feature
      ( B ) LOCATION: 1..20
      ( D ) OTHER INFORMATION: /product= "Synthetic DNA"
         / note= "In the primer sequence submitted N=inosine; and
         nucleotide # for the entire sequence is 2915-2934."

( x i ) SEQUENCE DESCRIPTION: SEQ ID NO:8:

TTNANNGCAT GNCCATTATT                                                                 20

( 2 ) INFORMATION FOR SEQ ID NO:9:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: Other nucleic acid ( i v ) ANTI-SENSE: YES ( i x ) FEATURE:
    ( A ) NAME/KEY: misc_feature
    ( B ) LOCATION: 1..20
    ( D ) OTHER INFORMATION: /product= "Synthetic DNA"
        / note= "In the primer sequence submitted N=inosine; and
        nucleotide # for the entire sequence is 2915-2934."

( x i ) SEQUENCE DESCRIPTION: SEQ ID NO:9:

TTNANNGCGT GNCCATTGTT  20

( 2 ) INFORMATION FOR SEQ ID NO:10:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: Other nucleic acid ( i v ) ANTI-SENSE: YES ( i x ) FEATURE:
    ( A ) NAME/KEY: misc_feature
    ( B ) LOCATION: 1..20
    ( D ) OTHER INFORMATION: /product= "Synthetic DNA"
        / note= "In the primer sequence submitted N=inosine; and
        nucleotide # for the entire sequence is 2915-2934."

( x i ) SEQUENCE DESCRIPTION: SEQ ID NO:10:

TTNANNGCGT GNCCATTATT  20

( 2 ) INFORMATION FOR SEQ ID NO:11:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: Other nucleic acid ( i v ) ANTI-SENSE: YES ( i x ) FEATURE:
    ( A ) NAME/KEY: misc_feature
    ( B ) LOCATION: 1..20
    ( D ) OTHER INFORMATION: /product= "Synthetic DNA"
        / note= "In the primer sequence submitted N=inosine; and
        nucleotide # for the entire sequence is 2915-2934."

( x i ) SEQUENCE DESCRIPTION: SEQ ID NO:11:

TTNANNGCGT GNCCGTTATT  20

( 2 ) INFORMATION FOR SEQ ID NO:12:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( i v ) ANTI-SENSE: YES ( i x ) FEATURE:
    ( A ) NAME/KEY: misc_feature
    ( B ) LOCATION: 1..20

(D) OTHER INFORMATION: /product= "Synthetic DNA"
/ note= "In the primer sequence submitted N=inosine; and nucleotide # for the entire sequence is 2915-2934."

(xi) SEQUENCE DESCRIPTION: SEQ ID NO:12:

TTNANNGCAT GNCCGTTATT  20

(2) INFORMATION FOR SEQ ID NO:13:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: Other nucleic acid (iv) ANTI-SENSE: NO (ix) FEATURE:
(A) NAME/KEY: misc_feature
(B) LOCATION: 1..20
(D) OTHER INFORMATION: /product= "Synthetic DNA"
/ note= "In the primer sequence submitted N=inosine; and nucleotide # for the entire sequence is 2852-2871."

(xi) SEQUENCE DESCRIPTION: SEQ ID NO:13:

TTCACATANT CNAGNTTTGA  20

(2) INFORMATION FOR SEQ ID NO:14:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: Other nucleic acid (iv) ANTI-SENSE: NO (ix) FEATURE:
(A) NAME/KEY: misc_feature
(B) LOCATION: 1..20
(D) OTHER INFORMATION: /product= "Synthetic DNA"
/ note= "In the primer sequence submitted N=inosine; and nucleotide # for the entire sequence is 2852-2871."

(xi) SEQUENCE DESCRIPTION: SEQ ID NO:14:

TTCACCTANT CNAGNTTTGA  20

(2) INFORMATION FOR SEQ ID NO:15:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: Other nucleic acid (iv) ANTI-SENSE: NO (ix) FEATURE:
(A) NAME/KEY: misc_feature
(B) LOCATION: 1..20
(D) OTHER INFORMATION: /product= "Synthetic DNA"
/ note= "In the primer sequence submitted N=inosine; and nucleotide # for the entire sequence is 2852-2871."

(xi) SEQUENCE DESCRIPTION: SEQ ID NO:15:

TTCACATANT CNCGNTTTGA  20

( 2 ) INFORMATION FOR SEQ ID NO:16:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Other nucleic acid ( i v ) ANTI-SENSE: NO ( i x ) FEATURE:
        ( A ) NAME/KEY: misc_feature
        ( B ) LOCATION: 1..20
        ( D ) OTHER INFORMATION: /product= "Synthetic DNA"
            / note= "In the primer sequence submitted N=inosine; and
            nucleotide # for the entire sequence is 2852-2871."

( x i ) SEQUENCE DESCRIPTION: SEQ ID NO:16:

TTCACATANT CNCGNTTCGA                  20

( 2 ) INFORMATION FOR SEQ ID NO:17:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Other nucleic acid ( i x ) FEATURE:
        ( A ) NAME/KEY: misc_feature
        ( B ) LOCATION: 1..20
        ( D ) OTHER INFORMATION: /product= "Synthetic DNA"
            / note= "In the primer sequence submitted N=inosine; and
            nucleotide # for the entire sequence is 2852-2871."

( x i ) SEQUENCE DESCRIPTION: SEQ ID NO:17:

TTCACATANT CNAGNTTCGA                  20

( 2 ) INFORMATION FOR SEQ ID NO:18:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Other nucleic acid ( i v ) ANTI-SENSE: NO ( i x ) FEATURE:
        ( A ) NAME/KEY: misc_feature
        ( B ) LOCATION: 1..20
        ( D ) OTHER INFORMATION: /product= "Synthetic DNA"
            / note= "In the primer sequence submitted N=inosine; and
            nucleotide # for the entire sequence is 2852-2871."

( x i ) SEQUENCE DESCRIPTION: SEQ ID NO:18:

TTCACCTANT CNCGNTTTGA                  20

( 2 ) INFORMATION FOR SEQ ID NO:19:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Other nucleic acid ( i v ) ANTI-SENSE: NO ( i x ) FEATURE:
    ( A ) NAME/KEY: misc_feature
    ( B ) LOCATION: 1..20
    ( D ) OTHER INFORMATION: /product= "Synthetic DNA"
        / note= "In the primer sequence submitted N=inosine
        residues; and nucleotide # for the entire sequence is
        2852- 2871."

( x i ) SEQUENCE DESCRIPTION: SEQ ID NO:19:

TTCACCTANT CNCGNTTCGA                            20

( 2 ) INFORMATION FOR SEQ ID NO:20:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: Other nucleic acid ( i v ) ANTI-SENSE: NO ( i x ) FEATURE:
    ( A ) NAME/KEY: misc_feature
    ( B ) LOCATION: 1..20
    ( D ) OTHER INFORMATION: /product= "Synthetic DNA"
        / note= "In the primer sequence submitted N=inosine
        residues; and nucleotide # for the entire sequence is
        2852- 2871."

( x i ) SEQUENCE DESCRIPTION: SEQ ID NO:20:

TTCACCTANT CNAGNTTCGA                            20

( 2 ) INFORMATION FOR SEQ ID NO:21:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: Other nucleic acid ( i v ) ANTI-SENSE: NO ( i x ) FEATURE:
    ( A ) NAME/KEY: misc_feature
    ( B ) LOCATION: 1..20
    ( D ) OTHER INFORMATION: /product= "Synthetic DNA"
        / note= "At position #2860 and position #2863 i=inosine
        residues; at position #2866 N=A or C or G or T; at
        position #2857 M=A or C; and nucleotide # for the entire
        sequence is 2852-2871."

( x i ) SEQUENCE DESCRIPTION: SEQ ID NO:21:

TTCACMTANT CNAGNTTTGA                            20

What is claimed is:

1. An isolated nucleic acid consisting of the nucleotide sequence set forth in the Sequence Listing as SEQ ID NO:1.

2. An isolated nucleic acid complementary to the nucleic acid fully of claim 1.

3. An isolated nucleic acid consisting of the nucleotide sequence set forth in the Sequence :Listing as SEQ ID NO:2.

4. An isolated nucleic acid complementary to the nucleic acid fully of claim 3.

5. A kit for detecting the nucleic acid of a poliovirus by nucleic acid amplification comprising a primer consisting of SEQ ID NO.:1 and a primer consisting of SEQ ID NO.:2.

* * * * *